(12) United States Patent
Taylor et al.

(10) Patent No.: US 7,828,150 B2
(45) Date of Patent: Nov. 9, 2010

(54) CONTAINER FOR MEDICAMENT POWDER

(75) Inventors: Anthony James Taylor, Ware (GB); Michael Harry Golden, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 504 days.

(21) Appl. No.: 10/276,932

(22) PCT Filed: Jun. 5, 2001

(86) PCT No.: PCT/EP01/06303

§ 371 (c)(1), (2), (4) Date: Nov. 20, 2002

(87) PCT Pub. No.: WO01/98174

PCT Pub. Date: Dec. 27, 2001

(65) Prior Publication Data

US 2003/0140923 A1  Jul. 31, 2003

(30) Foreign Application Priority Data

Jun. 21, 2000  (GB) .................. 0015043.3

(51) Int. Cl.
B65D 83/04 (2006.01)
(52) U.S. Cl. .................................... 206/539
(58) Field of Classification Search ......... None
See application file for complete search history.

(56) References Cited

U.S. PATENT DOCUMENTS

| | | | |
|---|---|---|---|
| 2,517,482 A * | 8/1950 | Hall .................. 128/203.15 |
| 2,524,162 A | 10/1950 | Chavannes et al. | |
| 3,333,683 A | 8/1967 | Scharre | |
| 3,371,825 A | 3/1968 | Cullen | |
| 3,670,874 A | 6/1972 | Brunner | |
| 3,704,806 A | 12/1972 | Plachenov et al. | |
| 3,738,540 A | 6/1973 | Morane | |
| 3,788,322 A | 1/1974 | Michaels | |
| 3,797,492 A | 3/1974 | Place | |
| 3,809,223 A | 5/1974 | Kendall | |
| 3,921,805 A | 11/1975 | Compere | |
| 4,042,170 A | 8/1977 | Ekman et al. | |

(Continued)

FOREIGN PATENT DOCUMENTS

CA  2099940  1/1994

(Continued)

OTHER PUBLICATIONS

Notice of Opposition to a European Patent EP1292510 (EP Counterpart to U.S. Appl. No. 10/276,932); Nov. 12, 2007.

(Continued)

*Primary Examiner*—Kevin T Truong
(74) *Attorney, Agent, or Firm*—Dwight S. Walker

(57) ABSTRACT

There is provided a container for a medicament powder formed from a material comprising a desiccant. In one embodiment the container is a medicament dispenser comprising a body defining a reservoir for medicament in powder form, and an outlet in communication with said reservoir. In another embodiment the container is a medicament dispenser comprising a body defining a chamber for receipt of a medicament carrier, and an outlet in communication with said chamber. Methods of controlling moisture flow are also described.

38 Claims, 7 Drawing Sheets

U.S. PATENT DOCUMENTS

| | | | |
|---|---|---|---|
| 4,135,622 A | | 1/1979 | Glick |
| 4,274,403 A | * | 6/1981 | Struve .................... 128/203.15 |
| 4,305,502 A | * | 12/1981 | Gregory et al. ............. 206/532 |
| 4,363,841 A | | 12/1982 | Snow |
| 4,429,792 A | * | 2/1984 | Machbitz .................... 206/531 |
| 4,447,565 A | | 5/1984 | Lula et al. |
| 4,449,632 A | | 5/1984 | Marusiak, Jr. |
| 4,509,196 A | | 4/1985 | Sak et al. |
| 4,570,820 A | | 2/1986 | Murphy |
| 4,645,073 A | | 2/1987 | Homan |
| 4,655,229 A | | 4/1987 | Sensabaugh, Jr. et al. |
| 4,664,256 A | | 5/1987 | Holskov |
| 4,702,963 A | | 10/1987 | Phillips et al. |
| 4,718,553 A | | 1/1988 | Adamoli et al. |
| 4,720,423 A | | 1/1988 | Fraser |
| 4,757,919 A | | 7/1988 | Smazik et al. |
| 4,769,395 A | | 9/1988 | Pauls |
| 4,802,583 A | | 2/1989 | Calvert et al. |
| 4,811,571 A | | 3/1989 | Mayer et al. |
| 4,815,602 A | | 3/1989 | Schirmer |
| 4,834,234 A | | 5/1989 | Sacherer et al. |
| 4,852,732 A | | 8/1989 | Wilski et al. |
| 4,861,632 A | | 8/1989 | Caggiano |
| 4,874,090 A | | 10/1989 | Dyke |
| 4,907,394 A | | 3/1990 | Tschepke et al. |
| 4,919,984 A | | 4/1990 | Maruhashi et al. |
| 4,938,238 A | | 7/1990 | Barnes et al. |
| 4,972,953 A | | 11/1990 | Friedman et al. |
| 4,988,558 A | | 1/1991 | Shigemoto |
| 5,035,935 A | | 7/1991 | Thomas et al. |
| 5,042,472 A | * | 8/1991 | Bunin .................... 128/203.15 |
| 5,062,569 A | | 11/1991 | Hekal |
| 5,073,599 A | | 12/1991 | Genske |
| 5,113,855 A | | 5/1992 | Newhouse |
| 5,126,123 A | | 6/1992 | Johnson |
| 5,186,775 A | | 2/1993 | Incorvia et al. |
| 5,192,548 A | * | 3/1993 | Velasquez et al. ........... 424/443 |
| 5,201,308 A | | 4/1993 | Newhouse |
| 5,270,305 A | | 12/1993 | Palmer |
| 5,279,421 A | | 1/1994 | Gouge et al. |
| 5,322,161 A | | 6/1994 | Shichman et al. |
| 5,394,868 A | | 3/1995 | Ambrosio et al. |
| 5,441,060 A | | 8/1995 | Rose et al. |
| 5,458,135 A | | 10/1995 | Patton et al. |
| 5,472,092 A | | 12/1995 | Evert |
| 5,522,385 A | | 6/1996 | Lloyd et al. |
| 5,524,613 A | | 6/1996 | Haber et al. |
| 5,551,557 A | | 9/1996 | Brooks et al. |
| 5,560,490 A | * | 10/1996 | Chawla ..................... 206/539 |
| 5,591,379 A | | 1/1997 | Shores |
| 5,617,845 A | | 4/1997 | Poss et al. |
| 5,619,984 A | | 4/1997 | Hodson et al. |
| 5,645,051 A | | 7/1997 | Schultz et al. |
| 5,678,538 A | | 10/1997 | Drought |
| 5,687,710 A | | 11/1997 | Ambrosio et al. |
| 5,687,746 A | * | 11/1997 | Rose et al. .................. 131/273 |
| 5,697,200 A | | 12/1997 | Insley et al. |
| 5,718,355 A | | 2/1998 | Garby et al. |
| 5,740,792 A | | 4/1998 | Ashley et al. |
| 5,740,793 A | | 4/1998 | Velasquez et al. |
| 5,743,398 A | | 4/1998 | Weder |
| 5,746,227 A | | 5/1998 | Rose et al. |
| 5,749,496 A | | 5/1998 | DeJonge et al. |
| 5,756,171 A | | 5/1998 | Moteki et al. |
| 5,763,028 A | | 6/1998 | Matsumoto et al. |
| 5,775,320 A | | 7/1998 | Patton et al. |
| 5,775,321 A | | 7/1998 | Alband |
| 5,779,122 A | | 7/1998 | Martinelli |
| 5,789,044 A | | 8/1998 | Ram et al. |
| 5,814,337 A | * | 9/1998 | Merrifield et al. ............ 424/466 |
| 5,829,434 A | | 11/1998 | Ambrosio et al. |
| 5,833,066 A | | 11/1998 | Hargus et al. |
| 5,833,093 A | | 11/1998 | Honaker et al. |
| 5,894,949 A | * | 4/1999 | Taskis et al. ................. 215/247 |
| 5,896,989 A | | 4/1999 | Ropiak et al. |
| 5,911,937 A | | 6/1999 | Hekal |
| 5,921,062 A | | 7/1999 | Weder |
| 5,924,417 A | * | 7/1999 | Braithwaite ............ 128/203.15 |
| 5,957,124 A | | 9/1999 | Lloyd et al. |
| 6,022,627 A | | 2/2000 | Weder |
| 6,029,661 A | | 2/2000 | Whaley et al. |
| 6,029,663 A | | 2/2000 | Eisele et al. |
| 6,039,718 A | | 3/2000 | Niedospial, Jr. |
| 6,050,400 A | | 4/2000 | Taskis et al. |
| 6,093,480 A | | 7/2000 | Eichbauer |
| 6,103,280 A | | 8/2000 | Molzahn et al. |
| 6,112,888 A | * | 9/2000 | Sauro et al. .................. 206/204 |
| 6,119,853 A | | 9/2000 | Garrill et al. |
| 6,131,566 A | | 10/2000 | Ashurst et al. |
| 6,179,118 B1 | | 1/2001 | Garrill et al. |
| 6,207,093 B1 | | 3/2001 | Hanyu et al. |
| 6,241,132 B1 | | 6/2001 | Morrison |
| 6,241,717 B1 | | 6/2001 | Niedospial, Jr. |
| 6,250,468 B1 | | 6/2001 | Huchel |
| 6,279,736 B1 | * | 8/2001 | Hekal ......................... 206/538 |
| 6,315,112 B1 | | 11/2001 | Garrill et al. |
| 6,328,032 B1 | | 12/2001 | Virtanen et al. |
| 6,328,327 B1 | | 12/2001 | Ligony |
| 6,352,152 B1 | | 3/2002 | Anderson et al. |
| 6,360,929 B1 | | 3/2002 | McCarthy |
| 6,390,291 B1 | * | 5/2002 | Garrill et al. ................. 206/204 |
| 6,484,718 B1 | | 11/2002 | Schaeffer et al. |
| 6,531,197 B2 | | 3/2003 | Neteler |
| 6,536,427 B2 | | 3/2003 | Davies et al. |
| 6,546,928 B1 | | 4/2003 | Ashurst et al. |
| 6,679,374 B2 | | 1/2004 | Garrill et al. |
| 6,737,044 B1 | | 5/2004 | Dickinson et al. |
| 2002/0048552 A1 | | 4/2002 | Garrill et al. |
| 2003/0198600 A1 | | 10/2003 | Akehurst et al. |
| 2003/0235664 A1 | | 12/2003 | Merical et al. |
| 2004/0097489 A1 | * | 5/2004 | Allen et al. .................. 514/220 |
| 2004/0131805 A1 | | 7/2004 | Merical et al. |
| 2006/0134007 A1 | | 6/2006 | Krueger et al. |
| 2006/0269708 A1 | | 11/2006 | Merical et al. |

FOREIGN PATENT DOCUMENTS

| | | | | |
|---|---|---|---|---|
| DE | 8605885 U1 | | 5/1986 | |
| DE | 4013799 | | 4/1990 | |
| DE | 19633495 | | 2/1998 | |
| DE | 19646048 | | 5/1998 | |
| EP | 0372777 | | 11/1989 | |
| EP | 0414536 | | 8/1990 | |
| EP | 0428380 | | 11/1990 | |
| EP | 0455463 | | 11/1991 | |
| EP | 0455463 A1 | | 11/1991 | |
| EP | 0688666 | | 12/1995 | |
| EP | 0793992 | | 9/1997 | |
| EP | 0938907 | | 9/1999 | |
| EP | 0990437 | | 4/2000 | |
| FR | 2812620 | * | 8/2000 | ................. 248/92 |
| GB | 1069929 | | 5/1967 | |
| GB | 1073786 | * | 6/1967 | ................. 206/461 |
| GB | 2140800 | | 12/1984 | |
| GB | 2222816 | | 3/1990 | |
| GB | 2272162 | | 5/1994 | |
| GB | 2306169 | | 4/1997 | |
| WO | 8901348 | | 2/1989 | |
| WO | 8912590 | | 12/1989 | |
| WO | 91/04011 | | 4/1991 | |
| WO | 91/11173 | | 8/1991 | |
| WO | 91/11495 | | 8/1991 | |
| WO | 91/14422 | | 10/1991 | |
| WO | 93/11743 | | 6/1993 | |

| | | | |
|---|---|---|---|
| WO | 9322215 | | 11/1993 |
| WO | 95/02651 | | 1/1995 |
| WO | 95/24889 | * | 9/1995 |
| WO | 95/32752 | | 12/1995 |
| WO | 95/34488 | | 12/1995 |
| WO | 96/04189 | | 2/1996 |
| WO | 96/09229 | | 3/1996 |
| WO | 96/26755 | | 9/1996 |
| WO | 96/29603 | | 9/1996 |
| WO | 96/32099 | | 10/1996 |
| WO | 96/32150 | | 10/1996 |
| WO | 96/32151 | | 10/1996 |
| WO | 96/32345 | | 10/1996 |
| WO | 9633108 | | 10/1996 |
| WO | 94/32663 | | 9/1997 |
| WO | 98/00352 A1 | | 1/1998 |
| WO | 9800352 A1 | | 1/1998 |
| WO | 98/41260 | | 9/1998 |
| WO | 98/41261 | | 9/1998 |
| WO | 99/32180 | * | 7/1999 ............ 128/203.12 |
| WO | 99/35039 | | 7/1999 |
| WO | 9932180 A1 | | 7/1999 |
| WO | 99/47195 | | 9/1999 |
| WO | 99/53901 | | 10/1999 |
| WO | 99/62697 | * | 12/1999 |
| WO | 00/37336 | | 6/2000 |
| WO | 00/37336 A1 | | 6/2000 |
| WO | 0037336 A1 | | 6/2000 |
| WO | 00/78861 | | 12/2000 |
| WO | 01/01921 | | 1/2001 |
| WO | 01/10742 | | 2/2001 |
| WO | 01/53079 | | 7/2001 |
| WO | 01/56895 | | 8/2001 |
| WO | 01/87731 | | 11/2001 |
| WO | WO2006/000758 | | 1/2006 |

OTHER PUBLICATIONS

MiniPax® product information by Multisorb Technologies, Copyright 2001; Nov. 2007.

Website print out relating to MiniPax® describing an event in Nov. 2000; Nov. 2007.

Excerpt from the DuPont website relating to TYVEX200 ; May 2007.

Multisorb Technologies, "MiniPax Sorbent Packets" www.multisorb.com, Nov. 13, 2007, pp. 92-93.

Multisorb Technologies, "Pack Expo International 2000" http://pei2000.packexpo.com/pei2000/exhibitors/exhibitor_display.cfm@companyID, Nov. 13, 2007, pp. 94-95.

Dupont TYVEK, "History", http://www2.dupont.com/Tyvek/en.US/products/about_pgs/history.html, Nov. 13, 2001, p. 100.

Jenkins, et al., "Packages Used for Pharmaceuticals", Packaging Drugs and Pharmaceuticals, 1993, pp. 254-258.

Aulton,"Pharmaceutics: The Science of Dosage Form Design", 1988, Packaging Technology, pp. 711-713.

O'Brien, "Packaging and converting technology" 1990, Medical Device Packaging Handbook, pp. 92-105.

Jenkins, et al., "The Fabrication and Filling of Pharmaceutical Containers",Packaging Drugs and Pharmaceuticals, 1993, pp. 148-152.

Summons to attend Oral Proceedings pursuant to Rule 115(1)EPC, European Patent Office, Jul. 18, 2010.

\* cited by examiner

CONTAINER FOR MEDICAMENT POWDER

This application is filed pursuant to 35 USC 371 as a United States National Phase Application of International Patent Application Serial No. PCT/EP01/06303 filed 5 Jun. 2001, which claims priority from GB 0015043 filed on 21 Jun. 2000 in the United Kingdom.

TECHNICAL FIELD

The present invention relates to containers and dispensers for medicament powders. In particular, the invention relates to dry powder inhalation dispensers and components thereof which substantially alleviate or reduce moisture build-up therein. The invention also relates to a method for reducing moisture ingress inside a dry powder inhaler.

BACKGROUND TO THE INVENTION

Medicaments for treating respiratory disorders are frequently administered as dry powder formulations through the mouth and nose. Dry powder medicament dispensers, such as inhalers, are used in the administration of these drugs, inhalation by the patient resulting in uptake of a specified dosage of medicament through the nose or mouth. The drug may be stored as a dry powder within a reservoir in the body of the inhaler, a metering chamber being utilised to administer a specified dose of medicament. Alternatively, more sophisticated medicament dispensers employ medicament carriers, such as individual capsules or blister packs/strips containing defined doses of powdered drug.

Patients often rely on medication delivered by dry powder inhalers for rapid treatment of respiratory disorders that are debilitating and in some cases life threatening. It is, therefore, essential that the prescribed dose of drug is delivered accurately and consistently to meet the patient's needs and comply with the requirements of regulatory authorities.

A problem which can occur in the storage and product lifetime of an inhaler is ingress of moisture into the medicament powder. A build-up of moisture can prevent the administration of an effective dose of medicament by causing an increase in particle size and/or adherence of hygroscopic particles to the walls of the carrier or device, thereby leading to reduced uptake via inhalation by the patient. In extreme cases, depending upon the chemical nature of the medicament, moisture build-up may lead to degradation of the drug.

Another problem can be microbial contamination, which is often assisted by the undesirable presence of excess moisture.

The Applicants have found that the inclusion of a desiccant in the body of the inhaler or the walls of the medicament carrier can significantly improve the aforementioned problems. Furthermore, storage of the inhaler or medicament carrier within a sealed is package incorporating a desiccant, can markedly reduce moisture ingress.

The Applicants has also found that the aforementioned problems can be ameliorated by controlling the ingress of moisture to, or egress of moisture from, the medicament container. Control may be achieved by either suitable choice of container materials or by enclosure of the container or a dispenser including the container in a suitable package. The control need not absolutely prevent moisture transfer. Indeed, the Applicants have found that under certain conditions a limited degree of moisture transfer can be desirable.

WO 99/32180 teaches the inclusion of moisture permeable chambers containing desiccants within a blister pack. U.S. Pat. No. 5,740,793 discloses the inclusion of a desiccant cartridge within an inhaler or the medicament carrier cassette. U.S. Pat. No. 5,394,868 describes a chamber within a powder inhaler for holding a desiccating substance. The use of desiccant filters within medicament dispensers is described in U.S. Pat. Nos. 5,687,746 and 5,775,320, and PCT patent application no. WO 89/01348.

SUMMARY OF INVENTION

According to the present invention, there is provided a container for a medicament powder formed from a material comprising a desiccant.

In one aspect, the container is suitable for containing a measured dose of medicament. Packs in blister pack form for the containment of a unit dose medicaments are envisaged, as are packs containing multiple unit dose blisters arranged sequentially or otherwise, such as in series form. A particular multi-unit dose arrangement comprises an elongate strip having multiple blisters arranged in series thereon.

In another aspect, the container is a reservoir for dry powder medicament. Metering means are provided to enable metering of dose from the reservoir and transport of that dose to a delivery position.

In one aspect, the container is a medicament dispenser comprising a body defining a reservoir for medicament in powder form, and an outlet in communication with said reservoir for release of the medicament. In one aspect, the device is an inhaler and the outlet is one through which a user can inhale.

In another aspect, the container is in the form of a reloadable cartridge comprising a medicament pack (e.g. in multi-unit dose blister form or reservoir form). The cartridge is shaped and sized for receipt by a medicament delivery device (e.g. an inhaler device).

In another aspect, the container is a medicament dispenser comprising a body defining a chamber for receipt of a medicament carrier, and an outlet in communication with said chamber for release of the medicament. In one aspect, the device is an inhaler and the outlet is one through which the user can inhale.

In yet another aspect, the body consists of the material comprising the desiccant.

In one aspect, the body comprises the material comprising the desiccant.

In another aspect, the material comprising the desiccant coats the body e.g. part or whole of the inside of the body.

In yet another aspect, the material comprising the desiccant is impregnated throughout the body.

In one aspect, the material comprising the desiccant lines the body (e.g. the interior of the body which contacts the medicament powder in use).

Optionally the desiccant comprising material may be located around a seal for sealing the reservoir or medicament carrier optionally the seal (e.g. in the form of a sealing ring) may itself comprise or consist of a desiccant.

In another aspect, the container is a medicament carrier.

In yet another aspect, the medicament carrier is a capsule comprising a wall enclosing the medicament.

In one aspect, the medicament carrier is a blister pack comprising a base sheet and a lid.

In another aspect, the medicament carrier comprises a material comprising a desiccant.

In yet another aspect, the material comprising the desiccant coats the wall, or the base sheet, or the lid of the medicament carrier.

In one aspect, the material comprising the desiccant impregnates the wall, or base sheet, or lid of the medicament carrier.

In another aspect, the material comprising the desiccant lines the wall, or base sheet, or lid of the medicament carrier.

In another aspect, the material comprising the desiccant is moulded into the wall, or base sheet, or lid of the medicament carrier.

In yet another aspect, a well containing desiccant surrounds individual pockets in the blister packs.

In one aspect, the blister pack comprises a laminate comprising a desiccant. Suitably, the laminate comprises material selected from the group consisting of metal foil, organic polymeric material and paper. Suitable metal foils include aluminium or tin foil having a thickness of from 5 to 100 µm, preferably from 10 to 50 µm, such as 20 to 30 µm. Suitable organic polymeric materials include polyethylene, polypropylene, polyvinyl chloride and polyethylene terephthalate.

Suitably, the base sheet and lid comprise different materials.

In another aspect, the material comprising the desiccant is an organic polymeric plastic having particular characteristics e.g. a thermoplastic.

In yet another aspect, the organic polymeric plastic is a polyamide.

Preferably the desiccant is selected from the group consisting of silica gel, zeolite, alumina, bauxite, anhydrous calcium sulphate, activated bentonite clay, water-absorbing clay, molecular sieve and any mixtures thereof.

In one aspect, the container additionally comprises a medicament in dry powder form. Suitably, the medicament is suitable for the treatment of respiratory disorders. Preferably, the medicament is salmeterol xinafoate, fluticasone propionate or a combination thereof.

In another aspect of the present invention there is provided a method of reducing water ingress into a medicament powder comprising using a container for a medicament powder according to any of the preceding claims.

In another aspect of the present invention there is provided a package for storage of a container for a medicament powder formed from a material capable of controlling the ingress of moisture thereto or egress or moisture therefrom.

In one aspect, the material is impermeable to moisture.

In another aspect, the material controls the ingress or egress of moisture such that the ambient moisture content within the package is essentially constant, such as varying by no more than ±20%, preferably by less than ±10%. Ambient moisture content may for example be measured by Relative Humidity within the package. The preferred absolute level of moisture content will vary from medicament to medicament but may be readily determined through laboratory testing.

In another aspect, the material enables moisture transfer in one way only i.e. ingress only or egress only.

In another aspect, the material enables moisture transfer to either a set minimum/maximum moisture content within the package or within a set minimum/maximum moisture transfer rate.

In another aspect, the material is also capable of controlling the flow of other gaseous or vapour form species. Tyvek (trade name) is a suitable material.

In one aspect, the package is wrappable and sealable around the container to form an enclosed volume in which the container is disposed, the package being impermeable to water vapour, thereby substantially reducing ingress of water vapour and particulate matter into said enclosed volume.

In another aspect, the package additionally comprises a desiccant within the enclosed volume.

Preferably the desiccant is selected from the group consisting of silica gel, zeolite, alumina, bauxite, anhydrous calcium sulphate, activated bentonite clay, water-absorbing clay, molecular sieve and any mixtures thereof.

In one aspect the package includes at least one heat sealable layer and at least one layer of a metal foil.

In another aspect, the metal comprising said metal foil is selected from the group consisting of aluminium, tin, iron, zinc and magnesium.

In yet another aspect, the package includes protective layers located on the outside of the package.

In one aspect, the protective layer comprises a polyester film and the heat sealable layer comprises an ionomer film.

In another aspect of the present invention there is provided a method of storing a container for a medicament powder comprising providing a packaging material which is capable of controlling the flow of water vapour; filling a container with a medicament powder; wrapping said container with said package material to form an enclosed volume in which said container is disposed therein; and sealing the package.

In yet another aspect, the method additionally comprises providing a desiccant within the enclosed volume.

In one aspect, the sealing comprises heat sealing said packaging material. In other aspects, the seal is formed by ultrasonic welding, heat stamping, adhesive or laser welding methods.

In another aspect of the present invention there is provided a packaged container, comprising a container containing a medicament powder; and an overwrap package enclosing the container and a desiccant; wherein the container and the desiccant are sealable within the overwrap. Preferably the overwrap comprises a desiccant material and/or is lined, coated or impregnated with a desiccant material.

The overwrap package may be in the form of a shrink wrap or of a loose wrap e.g. in sachet form. Any spare volume within the overwrap may be evacuated or an inert gas such as nitrogen deliberately inserted.

In another aspect of the present invention there is provided a packaged powder medicament dispenser (or reloadable cartridge therefor as described supra) comprising a medicament dispenser for a medicament powder; and an overwrap package enclosing the medicament dispenser, wherein the medicament dispenser are sealable within the overwrap. The overwrap package may comprise desiccant, and or the package may have desiccant contained therewithin. The medicament dispenser may comprise a powder reservoir or a medicament carrier for containment of medicament.

Where the overwrap comprises desiccant it may be impregnated or otherwise blended with material or added as a coating or a liner.

In another aspect, the body of said medicament dispenser also comprises a desiccant.

Preferably the desiccant is selected from the group consisting of silica gel, zeolite, alumina, bauxite, anhydrous calcium sulphate, activated bentonite clay, water-absorbing clay, molecular sieve, zinc chloride, and any mixtures thereof.

In another aspect of the present invention there is provided a container for a medicament powder formed from a material capable of controlling the ingress of moisture thereto or egress or moisture therefrom.

In one aspect, the material is impermeable to moisture.

In another aspect, the material controls the ingress or egress of moisture such that the ambient moisture content within the package is essentially constant, such as varying by no more than ±20%, preferably by less than ±10%.

In another aspect, the material enables moisture transfer in one way only i.e. ingress only or egress only.

In another aspect, the material enables moisture transfer to either a set minimum/maximum moisture content within the package or within a set minimum/maximum moisture transfer rate.

In another aspect, the material is also capable of controlling the flow of other gaseous or vapour form species.

In other aspects, the medicament container or overwrap therefor or any part of a medicament dispenser for use therewith is comprised of a material having desiccant blended or otherwise loaded or impregnated therein. Suitable materials are described in PCT Application Nos. WO99/62697 and WO/00/17258 in the name of Capitol Speciality Plastics Inc.

Suitable materials comprise a thermoplastic/desiccant blend. Examples of thermoplastics include polyolefin, polyethylene, polycarbonate, polyamide, ethylenevinyl acetate copolymer, ethylene-methacrylate copolymer, polyvinyl chloride, polystyrene, polyester, polyester amide, polyacrylic ester, and polyvinylidene chloride, acrylic, polyurethane, polyacetal, and polycarbonate. These and other thermoplastics may be utilized either singularly, or in combinations.

The concentration of desiccant entrained (e.g. mixed or blended) within the thermoplastic may exceed seventy-five percent (75%) to not greater than eighty percent (80%) by weight, so that about seventy-five percent (75%) may extend to eighty percent (80%) by weight. Typically, however, the desiccant concentration will fall within a range of forty to seventy-five percent (40-75%) desiccant to thermoplastic, by weight. This concentration is considered to be a high concentration for most thermoplastics. The maximum desiccant bearable concentrations will vary among the various types of thermoplastics due to their differing characteristics. In the instance of polyethylene or polypropylene, for example, the maximum concentration of desiccant will be about seventy-five percent (75%) by weight. As the desiccant concentrations within the thermoplastics increase, the performance of the material degenerates to unacceptable levels. At lower levels of desiccant concentrations, about forty percent (40%) could extend to as low as thirty percent (30%) where the limits of a viable product are reached.

BRIEF DESCRIPTION OF INVENTION

FIG. 2b is a top perspective of a medicament blister strip illustrated in FIG. 2a.

FIG. 3b is a top perspective of a medicament blister strip illustrated in FIG. 3a.

FIG. 4b is a top perspective of the medicament blister shown in FIG. 4a.

DETAILED DESCRIPTION OF THE DRAWINGS

Figure 1:
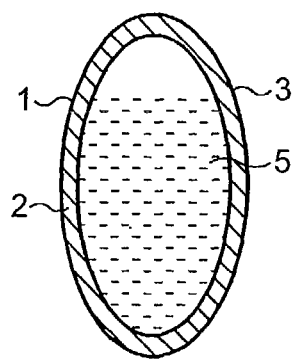
FIG. 1 shows a medicament carrier in the form of a capsule according to the present invention.

The medicament carrier in FIG. 1 is in the form of a capsule 1 comprising a wall 2 enclosing medicament powder 5. The wall 2 comprises a desiccant 3 which reduces or otherwise controls moisture ingress into the capsule 1 during storage and/or when in situ within the body of the inhaler (not shown). Medicament powder 5 is released on piercing the wall 2 of capsule 1 and may be inhaled by a patient.

Figure 2A:
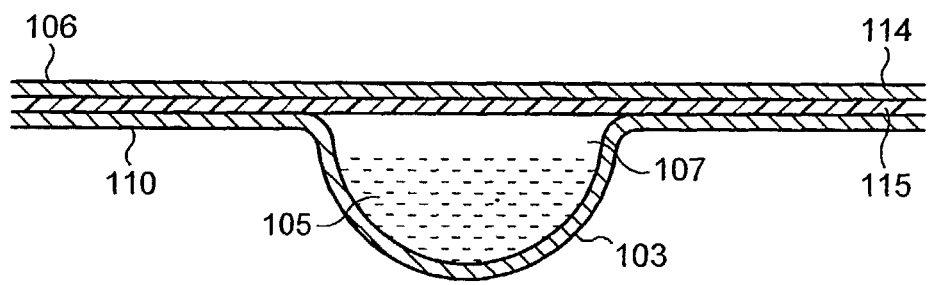
FIG. 2a is a cross-sectional side elevation of a single medicament blister strip impregnated with a desiccant according to the present invention.

FIG. 2a shows a sectional side-elevation of a single blister strip 106 comprising a pocket 107, containing dry powder 105, base 110 and lid comprising laminates 114, 115. The lid is composed of a metallic foil laminate 114 bound to a plastic laminate 115. In the diagram, the lid 114, 115 is hermetically sealed to base 110 by appropriate means (e.g. adhesion, welding). Base 110 comprises an organic polymeric plastic impregnated with desiccant 103. In use, the desiccant absorbs any moisture which permeates through the lid 114, 115 and base 110, maintaining the powder 105 in a dry condition until the lid 114, 115 is removed from the base 110.

Figure 2B:
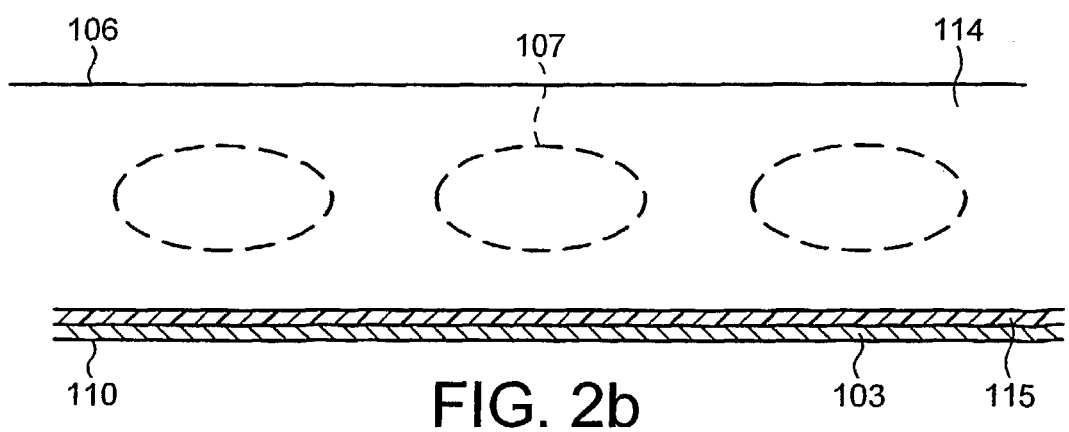

A top perspective of the blister strip 106 showing pockets 107 is illustrated in FIG. 2b. Laminated lid 114, 115 is sealed to base 110 which is impregnated with desiccant 103.

Figure 3A:
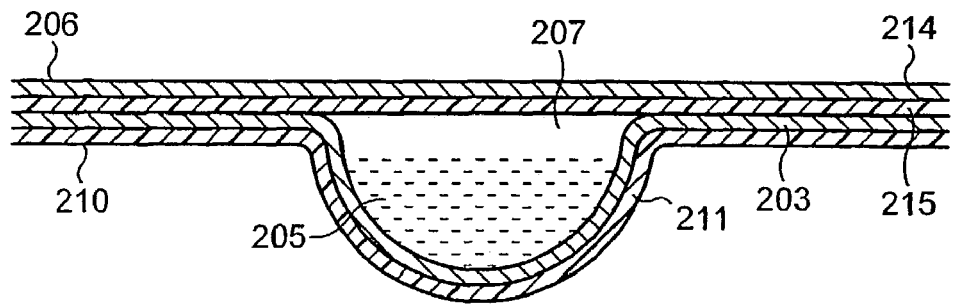
FIG. 3a is a cross-sectional side elevation of a single medicament blister having a laminate comprising a desiccant according to the present invention.

FIG. 3a shows a cross-sectional elevation of a different single blister strip 206 according to the invention. The blister strip 206 is composed of several laminated sheets, the lid being formed from metallic foil 214 and plastic laminate 215 while the base comprises plastic laminates 210 and 211. The plastic laminate 211 comprises a desiccant material 203 for absorbing any moisture which permeates through laminated sheets 214, 215 and 210, thereby reducing ingress into medicament powder 205 within pocket 207.

Figure 3B:
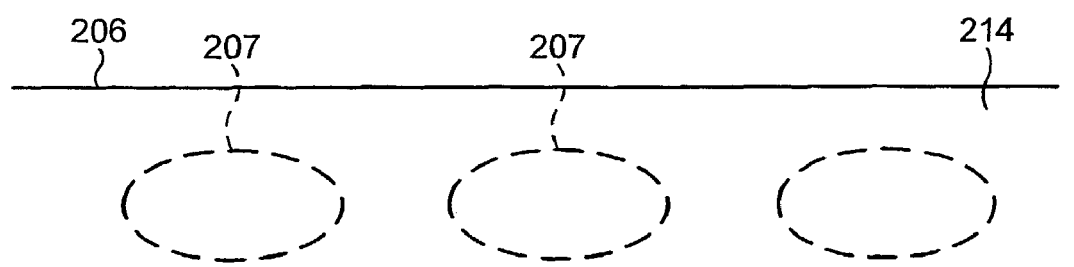
Figure 3B:
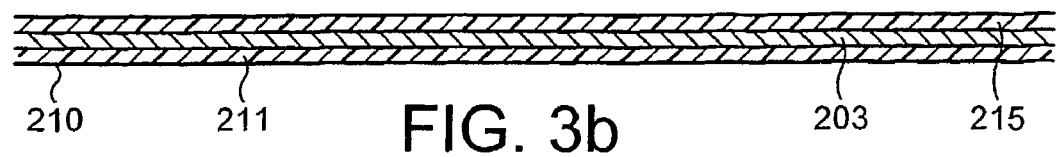

FIG. 3b is a top perspective of a blister strip 206 showing several blisters as described in FIG. 3a. Metallic foil 214 and plastic laminate 215 form a lid which is hermetically sealed, by appropriate adhesive or welding means, to the base of strip 206. The base comprises plastic laminates 210 and 211, laminate 211 being disposed on the internal surface of pocket 207 and comprising a desiccant.

Figure 4A:
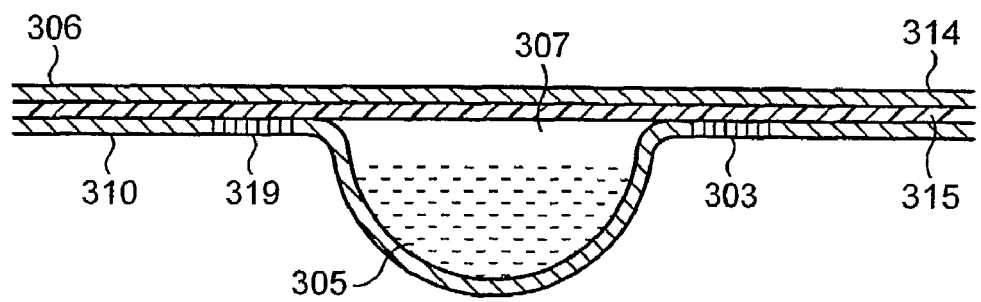
FIG. 4a is a cross-sectional side elevation of a single medicament blister having a ring containing a desiccant impregnated into the laminate surrounding the blister pocket.

FIG. 4a shows a cross-sectional elevation of yet another single blister strip 306 according to the invention. Metallic foil 314 and plastic laminate 315 form a lid for base 310 which are hermetically sealed together to reduce moisture ingress into pocket 307 containing medicament powder 305. The circumference of pocket 307 is surrounded by a ring 319, within base 310, comprising desiccant 303 which absorbs moisture which permeates into the blister, particularly between lid sheet 315 and base sheet 310.

Figure 4B:
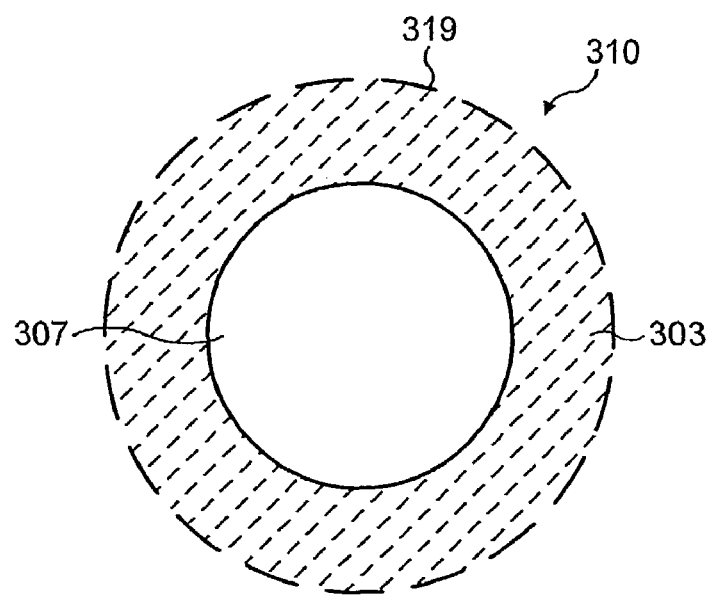

A plan perspective of the single blister strip 314 shown in FIG. 4a is illustrated in FIG. 4b. The ring 319 of material comprising desiccant 303 surrounds pocket 307 thereby absorbing any moisture which permeates into the pocket 307 through foil 314 and laminates 315 and/or base sheet 310, together with moisture ingress between lid and base sheets 315, 310.

Figure 5:
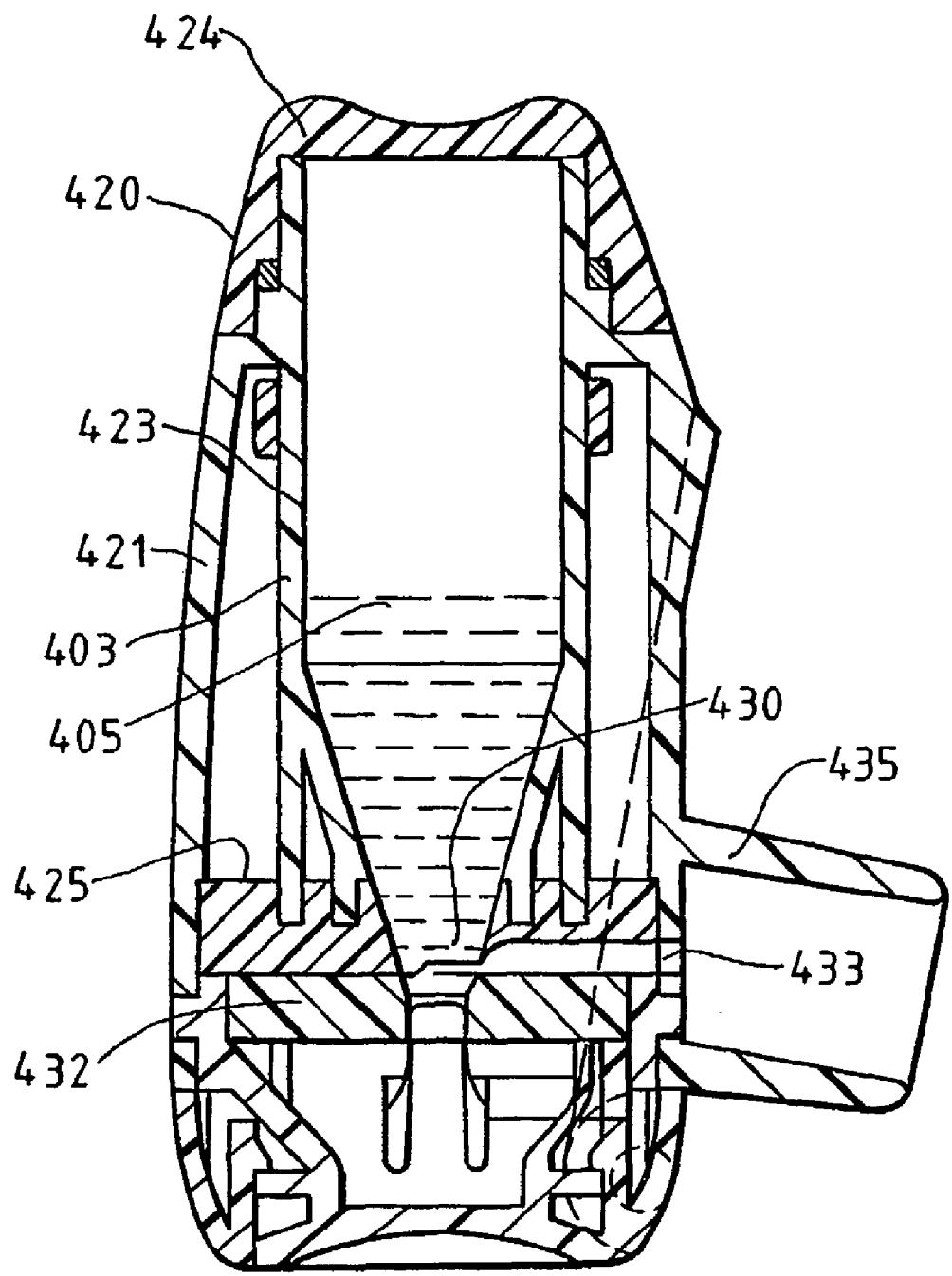
FIG. 5 shows a cross-sectional dry powder inhaler comprising a powder reservoir according the present invention.

FIG. 5 shows a sectional view of a dry powder inhaler 420 according to the present invention. The inhaler 420 comprises a body 421 which defines a reservoir 423 and a reservoir cover 424. The reservoir contains a supply of medicament in dry powder form 405. The walls 423 of the reservoir, defined by the body 421, are comprised of a desiccant material 403. Base 425 and body 421 define an aperture 430 through which powder 405 can pass from the reservoir to the dosing member 432. Powder 405 is guided by the walls 423 of the reservoir, which form a hopper, to the dosing member 432. Extending laterally from the lower end of the main body 421 is mouthpiece 435, through which the patient inhales via passage 433. If the device were intended for nasal inhalation this would be replaced by a nosepiece. The desiccant material 403, comprising walls 423, reduce moisture absorption by medicament powder 405. Optionally a desiccant comprising material may be located within the walls of passage 433 and/or a ring of same material around the metering valve (not shown) which controls the flow of medicament into passage 433.

Figure 6:
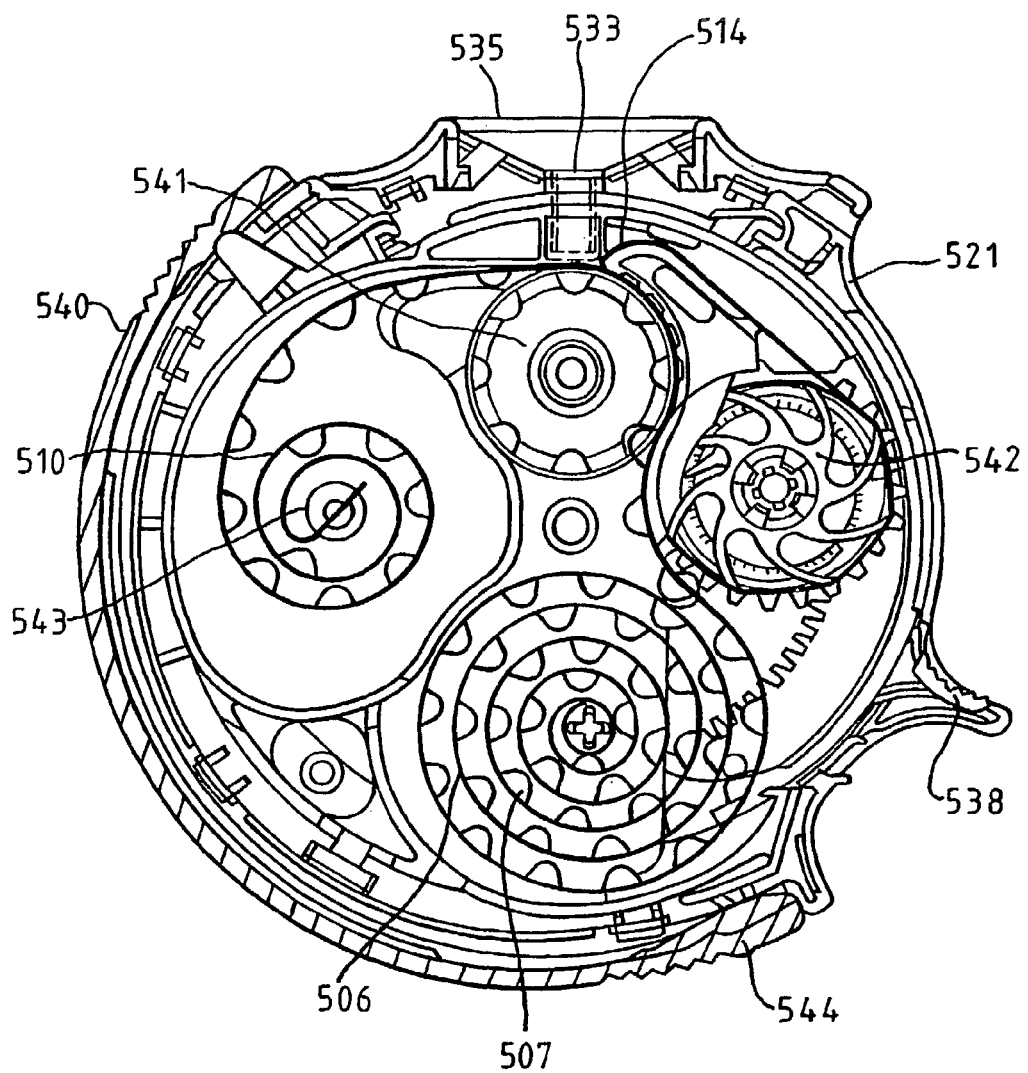
FIG. 6 shows a cross-sectional dry powder inhaler comprising a medicament carrier according to the present invention.

FIG. 6 shows a simplified cross-sectional plan view of a dry powder inhaler comprising a medicament carrier according to the present invention. The inhaler 540 dispenses unit doses of medicament powder from a medicament blister strip 506. The inhaler is comprised of an outer casing 544 enclosing a medicament strip 506 within body 521. The medicament strip may be, for example, any of those described in FIGS. 2a to 4b above. The internal walls of body 521 are comprised of a desiccant material (not shown) which reduce the levels of moisture within the internal cavity of the inhaler, thereby protecting the medicament powder within strip 506. The patient uses the inhaler by holding the device to his mouth, depressing lever 538, and inhaling through mouthpiece 535. Depression of lever 538 activates the internal mechanism of the inhaler, such that the lid 514 and base 510 sheets of coiled medicament blister strip 506 are separated at index wheel 541 by use of contracting wheel 542 and base wheel 543. A unit dose of powdered medicament within blister pocket 507 is released and may be inhaled by the patient through exit port 533 and mouthpiece 535.

Figure 7:
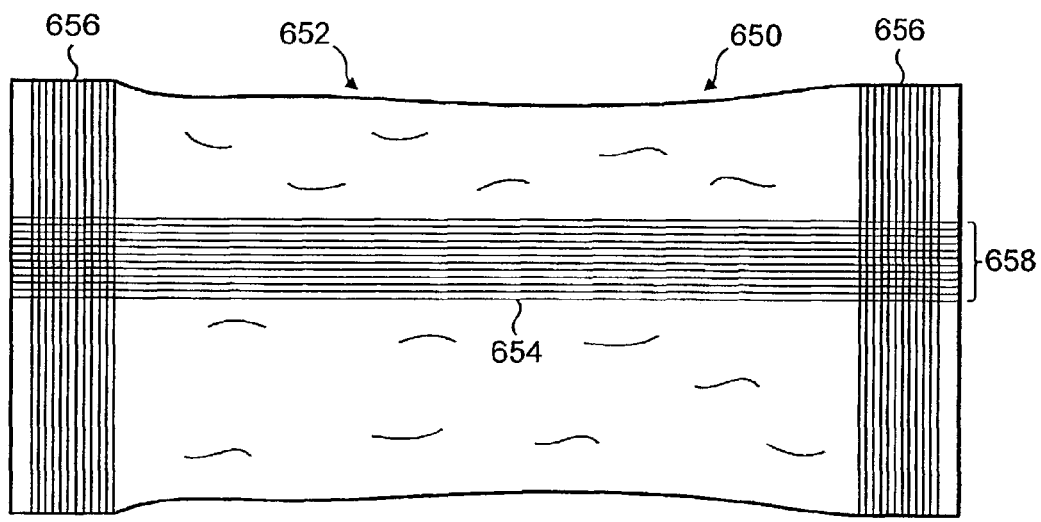
FIG. 7 is a top perspective of a package for storing a dry powder inhaler according to the present invention.

FIG. 7 shows a top perspective of a container storage system for storing a dry powder inhaler or cartridge refill therefor according to the present invention. The container storage system 650 includes a package or wrapping 652 that employs multi-layers of material 970, 972, 974. (See FIG. 10.) The package 652 further includes fin seams 654, 656 which are disposed along two parallel side edges of the package and along a single longitudinal edge of the package 652. The package 652 comprises a desiccant material, or alternatively is lined, coated or impregnated with a desiccant material.

The number and type of fin seams 654, 656 are not limited to the types shown in the drawings. The package 652 can include additional seams or significantly fewer seams such as a continuous single seam. The orientation of the seams 654, 656 is not limited to the orientation shown in the drawings. The orientation of the seams 654, 656 is typically a function of the sealing device and such seams may be oriented in a manner which substantially increases manufacturing efficiency. During manufacture, the longitudinal seam 654 may be formed first by heat sealing and the two end seams 656 may then be formed by heat sealing to close the package. Other types of seams include, but are not limited to, gusset type seams which include excess material which provides expansibility, stitched type seams, or mechanically crimped seams, and other like structures.

Figure 9:
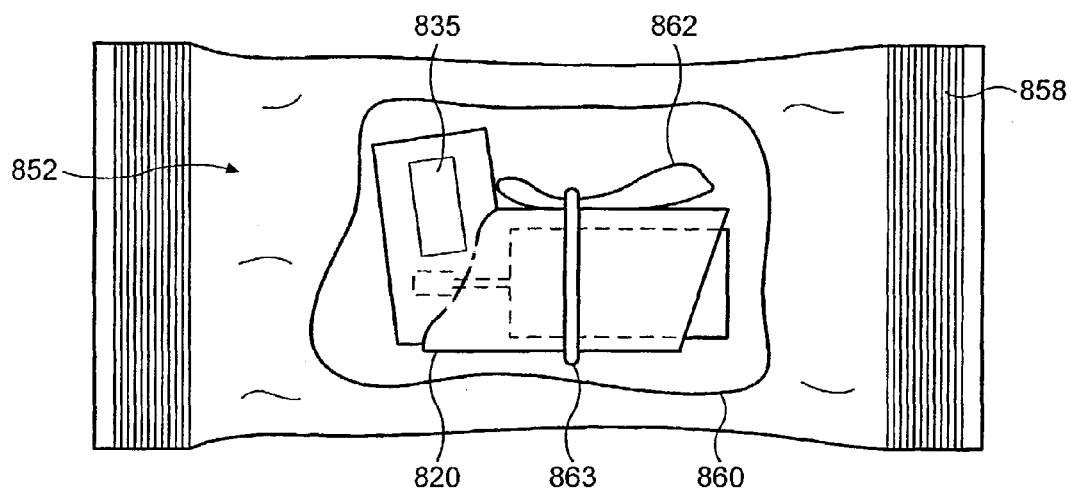
FIG. 9 is a cut-away bottom perspective of the package for storing a dry powder inhaler according to the present invention.

The container storage system includes a dry powder inhaler 820 (see FIG. 9). While the preferred inhaler is a dry powder inhaler 820, other dry powder inhalers (such as that described in FIG. 6) are not beyond the scope of the present invention.

Figure 8:
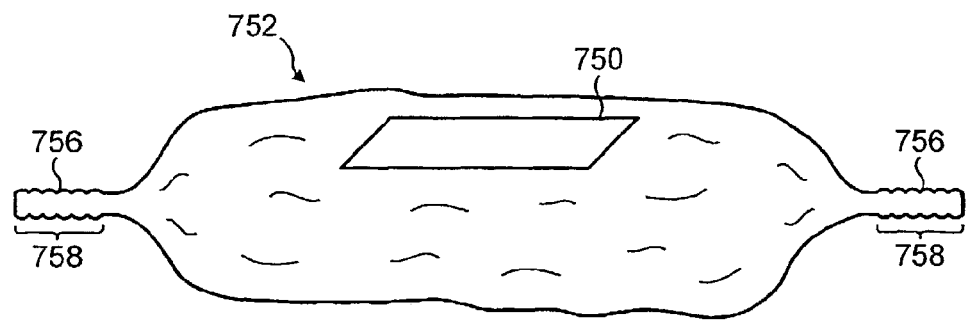
FIG. 8 is a side perspective of the package of FIG. 7.

FIG. 8 shows a side perspective of the container storage system of FIG. 7. The fin seams 654 and 656 in FIG. 7 are formed by a conventional heat sealing device which mechanically crimps sides of the package 750 together while simultaneously providing heat to the sides 654, 656/756 (FIGS. 7 and 8). The heat sealing device typically has electrical heater elements shaped to produce the pattern of the fin seams 654, 656/756 where the fin seams include multiple ridges 658/758. The sealing mechanism of the container storage system 650/750 of the present invention is not limited to heat sealing devices. Other sealing devices include, but are not limited to, glue sealing machines, sonic welding machines, electron beam radiation machines, and other like sealing devices.

As shown in FIG. 7, the package 750 preferably has a substantially rectangular configuration with a substantially elliptical cross section, however, other shapes of the package 750 are not beyond the scope of the present invention. Other shapes include, but are not limited to circular, square, triangular, trapezoidal, pentagonal, hexagonal, octagonal, and other like shapes. The shape of the package 750 is preferably a function of the shape of the enclosed medicament powder container 34 as well as the amount and type of storage space since the package 752 is made from flexible materials as will be described in further detail below.

FIG. 9 shows a cut-away bottom perspective of the package for storing a dry powder inhaler according to the present invention. The package 852 provides an enclosed volume 860 in which the inhaler 820 is disposed therein. The size of the enclosed volume 860 can be adjusted according to the size of the inhaler 820 and related parts thereto. Preferably, the enclosed volume 860 is of a size which permits relative ease of closing respective sides and layers 852, 26 and 28 without substantial stretching of the package 852. The enclosed volume 860 may be substantially evacuated prior to formation of the fin seams 858, 854 (not shown) to substantially reduce any water vapour being present in the enclosed volume 860. The enclosed volume 860 may be evacuated to such a degree that the enclosed volume 860 is a vacuum region around the medicament inhaler 820. While the enclosed volume 860, may remain constant, its relative shape may change according to shifting of the inhaler 820 disposed within the enclosed volume 860. In a preferred embodiment, a porous container of moisture absorbing material 862 lays adjacent to the mouthpiece 835 in a loose or free flowing manner. Alternatively, the moisture absorbing material 862 can be secured to the inside of the flexible package. In another alternative embodiment, the moisture absorbing container 862 may be attached to a bracket structure such as a ring which is fastened to the inhaler 820.

In one possible embodiment, the moisture absorbing material may be attached to the external surface of the mouthpiece 835 by a fastening device such as a rubber band 863. The fastening device 863 is preferably a removable elastic mechanism such as a rubber band. However, other fastening devices are not beyond the scope of the present invention. Other fastening devices include, but are not limited to, adhesives, adhesive tapes, shrink-wrap plastic, fasteners such as screws, nails, or rivets, compartments which are part of the mouthpiece housing 46, and other like attachment devices. In an alternative embodiment (not shown), a plurality of beads of material comprising a desiccant may be placed within the enclosed space 860. Similarly, other carriers comprised of a desiccant material may be enclosed within space 860 to absorb excess moisture from the enclosure.

Figure 10:
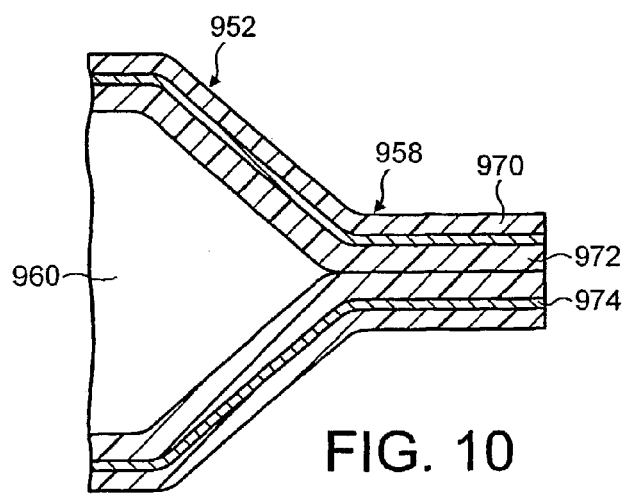
FIG. 10 is a cross-sectional view of the package for storing a dry powder inhaler according to the present invention.

FIG. 10 is a cross-sectional view of the package for storing a dry powder inhaler according to the present invention. The amorphous shape of the enclosed volume 960 is attributed to the flexible materials which make up the layers 970, 972, 974 of the package 952. The enclosed volume 960 can be varied in size such that it substantially conforms to the shape of the inhaler and any related parts thereto or such that the enclosed volume 960 is larger than the inhaler 820, as shown in FIG. 9. When the enclosed volume is of a size which is substantially equivalent with the surface area of the inhaler 820 and related parts, the layers 970, 972, and 974 of material substantially conform to the shape of the inhaler and related parts. The package is preferably placed in a separate, more rigid container, such as a paperboard or cardboard box (not shown) typically used in the pharmaceutical industry. The package may expand during storage due to slow leakage of volatiles from the plastics constituting the body of the inhaler. In this situation, the shape of the package may conform to some extent to the internal shape of the rigid container if the volume of the rigid container is just slightly larger than the expanded volume of the flexible package.

Flexible Packaging Materials

The flexible packaging material can be any material which is impervious to or substantially impervious to moisture. The packaging material is preferably permeable to volatiles which may escape from the plastics forming the body of the inhaler and/or the medicament carrier, by diffusion or otherwise, thereby preventing a build-up in pressure.

For ease of manufacturing, and in order to provide the necessary properties to the packaging material, the flexible packaging material preferably comprises a non-thermoplastic substrate (such as a metal foil) and a heat sealable layer disposed thereon, and an additional protective layer, such as a polymer film of polyester. The heat sealable layer is usually disposed on the inner surface of the assembled package. The additional protective layer is usually disposed on the surface opposite the heat sealable layer. An example of a particularly useful foil laminate is a polyester film adhesively laminated to aluminium foil adhesively laminated to Ionomer (SURLYN™) film, for example, 12μ polyester/9μ aluminum/50μ ionomer film supplied by Lawson Mardon Singen (LMS). To further reduce moisture ingress, thicker metal films, such as 20 to 25μ, may be used.

The substrate is preferably formed from aluminium foil. However, other metals for the substrate include, but are not limited to, tin, iron, zinc, or magnesium formed on a sheet by vacuum deposition or sputtering and a carboxyl group-containing polyolefin layer formed on the metal layer by lamination.

The heat sealable layer can be formed from any thermoplastic or thermosetting material such as an ionomer resin, polyolefin, or cycloolefin copolymer. Ionomer resins typically include ionically cross-linked ethylene-methacrylic acid and ethylene acrylic acid copolymers. Properties which distinguish these ionomers resins from other polyolefin heat-sealed polymers are high clarity, high impact resistance, low haze in lamination, tear resistance, abrasion resistance, solid state toughness, and moisture imperviousness. In the preferred embodiment, the heat sealable layer is made out of SURLYN™ (an ionomer resin) or a form of polyethylene to provide sufficient heat sealing properties.

The outer protective layer, if present, can be formed of any material as long as the final laminate has the requisite properties.

Preferably, the protective layer (e.g., polyester) is adhesively laminated to the substrate (e.g., aluminium) and the substrate layer in turn is adhesively laminated to the heat sealable layer (e.g., the ionomer film or SURLYN™ (an ionomer resin)). Preferred exemplary thicknesses of the three layers include a protective layer 1 to 40, preferably 4 to 30, more preferably 10 to 23 microns, and most preferably 12 microns; a substrate layer of 1 to 100, preferably 3 to 70, more preferably 5 to 50 microns, more preferably 6 to 20 microns, and most preferably 9 microns. For the heat sealable layer, preferred exemplary thicknesses include thicknesses of 1 to 100, preferably 5 to 70, more preferably 10 to 60, more preferably 20 to 55 microns, and most preferably 50 microns.

Adhesives may be used to join the respective layers of materials together. The adhesive layers are typically substantially smaller in thickness relative to the thickness of the substrate, heat sealable and/or protective layers which they bond. The number, size, and shape of the layers are not limited to those layers shown in the drawings. Any number of layers with relative areas of any size and predetermined thicknesses may be used so long as the flexible package forms an enclosed volume which substantially prevents ingression of water vapour and particulate matter into the enclosed volume while permitting egression out of the enclosed volume of any volatile released from the plastics used in the body of the inhaler or the medicament carrier. The size, shape, and number of layers of the package are typically a function of the size and contents of the inhaler and/or medicament carrier.

The package is believed to operate similarly to a virtual one-way valve due to the composition of the layers and due to the transmission rate of water vapour molecules into the enclosed volume relative to the transmission rate of gas molecules of a plastic volatile, such as formaldehyde, out of the enclosed volume. The package permits the volatile to diffuse out of the enclosed volume while substantially preventing water vapour and other particulate matter from entering the enclosed volume. Excess or leakage of the volatile is permitted to egress from the package. The virtual one-way valve function of the package prevents or minimizes the chance of any sudden ruptures or prevents or minimizes unexpected expulsion of the plastic volatile during opening of the package.

Moisture Absorbing Materials

The moisture absorbing material is preferably a silica gel desiccant sachet. However, other vapour or moisture absorbing mechanisms are not beyond the scope of the present invention. Other vapour or moisture absorbing materials include desiccants made from inorganic materials such a zeolites and aluminas. Such inorganic materials of vapour or moisture absorbing materials have high water absorption capacities and favourable water absorption isotherm shapes. The water absorption capacity of such materials typically varies from 20 to 50 weight percent. In the preferred embodiment, the absorbing material is a MINIPAX® supplied by Multisorb Technologies in the United States and Silgelac in Europe (silica gel packaged inside TYVEK®, which is a nylon mesh bonded with a microporous polyurethane). Other exemplary moisture absorbing materials include, but are not limited to, alumina, bauxite, anhydrous, calcium sulphate, water-absorbing clay, activated bentonite clay, a molecular sieve, or other like materials which optionally include a moisture sensitive colour indicator such as cobalt chloride to indicate when the desiccant is no longer operable. While in the preferred embodiment of the present invention, the package is designed to substantially prevent ingression of water vapour and particulate matter into the enclosed volume, the moisture absorbing material is placed within the enclosed volume in order to absorb any residual moisture present in the atmosphere or on the external surface of the pressurized container or mouthpiece or a combination thereof, prior to sealing the package.

The desiccant should be present in an amount sufficient to absorb any residual moisture inside the package. When silica gel is used, 1 g to 10 g of silica gel is sufficient for a typical dry powder inhaler. Moreover, the desiccant should be present in an amount sufficient to absorb any moisture that possibly ingresses from the external environment. It is also possible to place the desiccant inside the container, either loose in the canister or as part of an assembly attached to the canister.

Medicaments

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (eg s the sodium salt), ketotifen or nedocromil (eg as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (eg as the dipropionate ester), fluticasone (eg as the propionate ester), flunisolide, budesonide, rofleponide, mometasone eg as the furoate ester), ciclesonide, triamcinolone (eg as the acetonide) or 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (eg as free base or sulphate), salmeterol (eg as xinafoate), ephedrine, adrenaline, fenoterol (eg as hydrobromide), formoterol (eg as fumarate), isoprenaline, metaproterenol, phenylephrine, phenylpropanolamine, pirbuterol (eg as acetate), reproterol (eg as hydrochloride), rimiterol, terbutaline (eg as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, eg 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); α$_4$ integrin inhibitors eg (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g as free acid or potassium salt), diuretics, e.g., amiloride; anticholinergics, e.g., ipratropium (eg as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (eg as the fumarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

It may be appreciated that any of the parts of the medicament container used therewith which contact the medicament may be coated with materials such as fluoropolymer materials which reduce the tendency of medicament to adhere thereto. Suitable fluoropolymers include polytetrafluoroethylene (PTFE) and fluoroethylene propylene (FEP). Any movable parts may also have coatings applied thereto which enhance their desired movement characteristics. Frictional coatings may therefore be applied to enhance frictional contact and lubricants used to reduce frictional contact as necessary.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A medicament carrier adapted for use in a dry powder inhaler, wherein the medicament carrier is a laminate multi-unit blister pack comprising a base sheet, in which are formed multiple pockets in series arrangement, each pocket containing a dose of inhalable dry powder medicament in free contact with the base sheet, and a lid to cover the multiple pockets, wherein the laminate multi-unit blister pack includes a metal foil and a layer of an organic polymeric plastic material comprising a desiccant impregnated therein.

2. The carrier according to claim 1, wherein the laminate multi-unit blister pack additionally comprises a paper material.

3. The carrier according to claim 1, wherein the metal foil is an aluminum or tin foil having a thickness of from 5 to 100 μm.

4. The carrier according to claim 1, wherein the organic polymeric plastic material is selected from the group consisting of polyethylene, polypropylene, polyvinyl chloride and polyethylene terephthalate.

5. The carrier according to claim 1, wherein the desiccant is selected from the group consisting of silica gel, zeolite, alumina, bauxite, anhydrous calcium sulphate, activated bentonite clay, water-absorbing clay, molecular sieve and any mixtures thereof.

6. The carrier according to claim 1, wherein the base sheet has the layer of the organic polymeric plastic material comprising the desiccant impregnated therein.

7. The carrier according to claim 6, wherein the layer of the organic polymeric plastic material comprising the desiccant impregnated therein is the innermost layer of the base sheet.

8. The carrier according to claim 6, wherein the organic polymeric plastic material is selected from the group consisting of polyethylene, polypropylene, polyvinyl chloride and polyethylene terephthalate.

9. The carrier according to claim 6, wherein the desiccant is selected from the group consisting of silica gel, zeolite, alumina, bauxite, anhydrous calcium sulphate, activated bentonite clay, water-absorbing clay, molecular sieve and any mixtures thereof.

10. The carrier according to claim 6, wherein the lid includes the metal foil.

11. The carrier according to claim 1, wherein the medicament is suitable for the treatment of respiratory disorders.

12. The carrier according to claim 1, wherein said medicament is salmeterol xinafoate.

13. The carrier according to claim 1, wherein said medicament is fluticasone propionate.

14. The carrier according to claim 1, wherein said medicament is a combination of salmeterol xinafoate and fluticasone propionate.

15. A dry powder inhaler which contains a carrier according to claim 1 and which is configured and arranged to open the at least one pocket to enable dispensing of the powder from the inhaler.

16. A medicament carrier adapted for use in a dry powder inhaler, wherein the medicament carrier is a laminate multi-unit blister pack comprising a base sheet, in which are formed multiple pockets in series arrangement, each pocket containing a dose of inhalable dry powder medicament in free contact with the base sheet, and a lid to cover the multiple pockets, wherein the laminate multi-unit blister pack includes a metal foil and wherein the base sheet has a layer of an organic polymeric plastic material comprising a desiccant impregnated therein.

17. The carrier according to claim 16, wherein the laminate multi-unit blister pack additionally comprises a paper material.

18. The carrier according to claim 16, wherein the metal foil is an aluminium or tin foil having a thickness of from 5 to 100 μm.

19. The carrier according to claim 16, wherein the organic polymeric plastic material is selected from the group consisting of polyethylene, polypropylene, polyvinyl chloride and polyethylene terephthalate.

20. The carrier according to claim 16, wherein the desiccant is selected from the group consisting of silica gel, zeolite, alumina, bauxite, anhydrous calcium sulphate, activated bentonite clay, water-absorbing clay, molecular sieve and any mixtures thereof.

21. The carrier according to claim 16, wherein the layer of the organic polymeric plastic material comprising the desiccant impregnated therein is the innermost layer of the base sheet.

22. The carrier according to claim 16, wherein the lid includes the metal foil.

23. The carrier according to claim 16, wherein the medicament is suitable for the treatment of respiratory disorders.

24. The carrier according to claim 16, wherein said medicament is salmeterol xinafoate.

25. The carrier according to claim 16, wherein said medicament is fluticasone propionate.

26. The carrier according to claim 16, wherein said medicament is a combination of salmeterol xinafoate and fluticasone propionate.

27. A multiple unit dose dry powder inhaler which contains therein a carrier according to claim 16 and which is configured and arranged to open the pockets of the medicament carrier to enable a unit dose of the powder to be repeatedly dispensed from the inhaler.

28. A medicament carrier adapted for use in a dry powder inhaler, wherein the medicament carrier is a laminate multi-unit blister pack comprising a base sheet, in which are formed multiple pockets in series arrangement, each pocket containing a dose of inhalable dry powder medicament in free contact with the base sheet, and a lid to cover the at least one pocket, wherein the base sheet and the lid of the laminate multi-unit blister pack include a metal foil, and wherein the base sheet has a layer of an organic polymeric plastic material comprising a desiccant impregnated therein.

29. The carrier according to claim 28, wherein the laminate blister pack additionally comprises a paper material.

30. The carrier according to claim 28, wherein the metal foil is an aluminium or tin foil having a thickness of from 5 to 100 μm.

31. The carrier according to claim 28, wherein the organic polymeric plastic material is selected from the group consisting of polyethylene, polypropylene, polyvinyl chloride and polyethylene terephthalate.

32. The carrier according to claim 28, wherein the desiccant is selected from the group consisting of silica gel, zeolite, alumina, bauxite, anhydrous calcium sulphate, activated bentonite clay, water-absorbing clay, molecular sieve and any mixtures thereof.

33. The carrier according to claim 28, wherein the layer of the organic polymeric plastic material comprising the desiccant impregnated therein is the innermost layer of the base sheet.

34. The carrier according to claim 28, wherein the medicament is suitable for the treatment of respiratory disorders.

35. The carrier according to claim 28, wherein said medicament is salmeterol xinafoate.

36. The carrier according to claim 28, wherein said medicament is fluticasone propionate.

37. The carrier according to claim 28, wherein said medicament is a combination of salmeterol xinafoate and fluticasone propionate.

38. A multiple unit dose dry powder inhaler which contains a carrier according to claim 28 and which is configured and arranged to open the pockets of the medicament carrier to enable a unit dose of the powder to be repeatedly dispensed from the inhaler.

* * * * *